US010020175B2

(12) United States Patent
Krause

(10) Patent No.: US 10,020,175 B2
(45) Date of Patent: Jul. 10, 2018

(54) MULTIPLE OIL-EMISSION MEASURING DEVICE FOR ENGINES

(71) Applicant: Lubrisense GmbH, Hamburg (DE)

(72) Inventor: Sven Krause, Bendestorf (DE)

(73) Assignee: Lubrisense GmbH, Hamburg (DE)

(*) Notice: Subject to any disclaimer, the term of this patent is extended or adjusted under 35 U.S.C. 154(b) by 0 days.

(21) Appl. No.: 15/023,638

(22) PCT Filed: Sep. 18, 2014

(86) PCT No.: PCT/EP2014/069919
§ 371 (c)(1),
(2) Date: Mar. 21, 2016

(87) PCT Pub. No.: WO2015/040124
PCT Pub. Date: Mar. 26, 2015

(65) Prior Publication Data
US 2016/0211127 A1 Jul. 21, 2016

(30) Foreign Application Priority Data

Sep. 20, 2013 (DE) ........................ 10 2013 218 930

(51) Int. Cl.
*H01J 49/04* (2006.01)
*G01N 1/22* (2006.01)
(Continued)

(52) U.S. Cl.
CPC ....... *H01J 49/0422* (2013.01); *G01M 15/102* (2013.01); *G01N 1/22* (2013.01);
(Continued)

(58) Field of Classification Search
CPC ..... G01M 15/102; G01N 1/22; G01N 1/2252; G01N 33/28; G01N 33/2817; H01J 49/0422; H01J 49/26
See application file for complete search history.

(56) References Cited

U.S. PATENT DOCUMENTS

| 7,372,043 B2 * | 5/2008 | Joyce | ................ H01J 49/0422 |
| | | | 250/281 |
| 7,564,027 B2 * | 7/2009 | Finch | ................ G01N 1/2214 |
| | | | 250/281 |

(Continued)

FOREIGN PATENT DOCUMENTS

| DE | 24 38 810 | 3/1976 |
| DE | 10 2004 001 514 | 8/2005 |

(Continued)

OTHER PUBLICATIONS

Behn, Andreas et al. (Jun. 2013). "System for the Measurement of Oil Emissions in Diesel Exhaust," Measuring Techniques 74(5). 424-429.

(Continued)

*Primary Examiner* — Harshad R Patel
*Assistant Examiner* — Punam Roy
(74) *Attorney, Agent, or Firm* — Morrison & Foerster LLP

(57) ABSTRACT

A multiple oil-emission device for hydrocarbon emissions in an exhaust-gas mixture, comprising an exhaust-gas probe, which has a transfer capillary, and a measurement channel, which has an ion source and a filter apparatus having a measuring apparatus. The transfer capillary has a drop-catching apparatus at the tip of the transfer capillary, which drop-catching apparatus comprises a short throttle segment and a transfer segment, which adjoins the throttle segment in a flow direction and is at least ten times longer. The measuring apparatus is connected to an analysing apparatus, which comprises a classifier for vaporous oil constituents and oil constituents in the form of drops. The classifier makes possible a differentiation between vaporous constituents and constituents in the form of drops, which makes robust and accurate determination possible regardless of the (Continued)

operating point because of the collection of constituents in the form of drops.

24 Claims, 3 Drawing Sheets

(51) Int. Cl.
H01J 49/26 (2006.01)
G01N 33/28 (2006.01)
G01M 15/10 (2006.01)

(52) U.S. Cl.
CPC .......... *G01N 1/2252* (2013.01); *G01N 33/28* (2013.01); *G01N 33/2817* (2013.01); *H01J 49/26* (2013.01)

(56) References Cited

U.S. PATENT DOCUMENTS

| | | | | |
|---|---|---|---|---|
| 7,642,510 B2* | 1/2010 | McEwen | ............ | H01J 49/0422 250/288 |
| 8,586,915 B2* | 11/2013 | Correale | ............ | G01N 1/2202 250/281 |
| 8,664,593 B2* | 3/2014 | Prasad | ................ | G01N 27/624 250/281 |
| 8,859,960 B2* | 10/2014 | Prasad | ................ | G01N 27/624 250/281 |
| 8,907,275 B1* | 12/2014 | Vidal-de-Miguel | .. | H01J 49/004 250/281 |
| 9,177,775 B2* | 11/2015 | Hasegawa | ........... | H01J 49/0431 |
| 9,252,004 B2* | 2/2016 | Otsuka | ................... | H01J 49/10 |
| 9,390,901 B2* | 7/2016 | Kertesz | ................... | H01J 49/04 |
| 2008/0210855 A1 | 9/2008 | Gohl et al. | | |
| 2011/0174966 A1* | 7/2011 | Wollnik | ................. | H01J 49/10 250/286 |
| 2014/0048699 A1* | 2/2014 | Ratner | ................. | G01N 33/483 250/282 |
| 2014/0084154 A1* | 3/2014 | Bazhenov | ................ | B01D 1/00 250/288 |
| 2015/0311055 A1* | 10/2015 | Otsuka | .................... | H01J 49/10 250/288 |
| 2016/0181082 A1* | 6/2016 | Covey | .................... | H01J 49/165 250/424 |
| 2016/0300703 A1* | 10/2016 | Hasegawa | .............. | G01N 27/62 |
| 2016/0329198 A1* | 11/2016 | Badu-Tawiah | ...... | H01J 49/0404 |
| 2017/0011902 A1* | 1/2017 | Gohl | ....................... | H01J 49/00 |

FOREIGN PATENT DOCUMENTS

| | | |
|---|---|---|
| DE | 10 2009 020 360 | 11/2010 |
| DE | 10 2010 012 606 | 9/2011 |
| EP | 0 577 543 | 1/1994 |
| GB | 2 245 188 | 1/1992 |

OTHER PUBLICATIONS

Krause, Sven. (Apr. 2009). "Massenspektrometrisches Verfahren Zur Charakterisierung der Ölverdampfung im Brennraum Von Ottomotoren", located at URL:http://d-nb.info/996706453/34, retrieved on Oct. 29, 2014; 145 pages with English translation of relevant sections.

International search report dated Nov. 6, 2014, directed to PCT Application No. PCT/EP2014/069919; 11 pages.

International Preliminary Report on Patentability dated Mar. 22, 2016, directed to PCT Application No. PCT/EP2014/069919; 8 pages.

\* cited by examiner

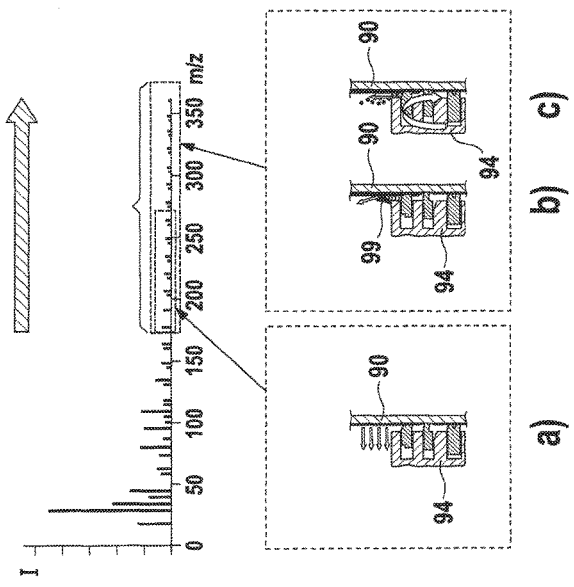
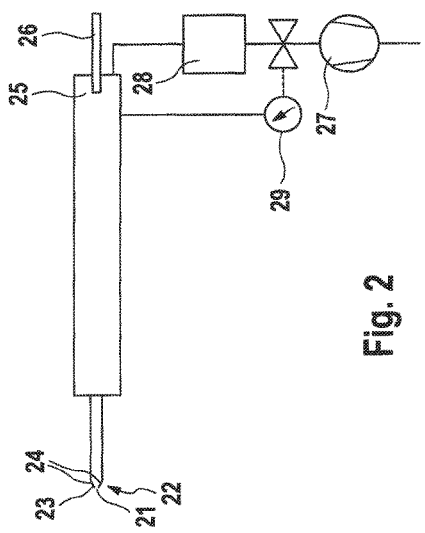
Fig. 2
Fig. 3

MULTIPLE OIL-EMISSION MEASURING DEVICE FOR ENGINES

CROSS-REFERENCE TO RELATED APPLICATIONS

This application is a national stage application under 35 USC 371 of International Application No. PCT/EP2014/069919, filed Sep. 18, 2014, which claims priority to German Application No. 10 2013 218 930.3, filed Sep. 20, 2013, the entire contents of which are incorporated herein by reference.

FIELD OF THE INVENTION

The invention relates to a multiple oil-emission measuring device for hydrocarbon emissions, as are discharged in particular by engines. The multiple oil-emission measuring device comprises an exhaust-gas probe for taking a sample amount, a measuring channel with a transfer capillary, an ion source and also a measuring device, which, as a broadband measuring device, carries out a global measurement over a mass spectrum.

BACKGROUND OF THE INVENTION

The reduction of harmful emissions from engines (or other systems converting thermal energy to mechanical energy) plays an important role in efforts to meet ever more demanding environmental protection requirements. Apart from emissions from the combustion process itself, this also concerns emissions produced by subsidiary processes in or on the engine. They may be not only emissions that can be regarded as reactants of the combustion process but also emissions that result from amounts of oil entering the exhaust gas of the engine, whether due to being scraped off from walls or entering in the form of vapors or droplets. In order to be able to achieve a reduction in the emissions, it is required to detect and assess the nature and type of emissions. For this purpose, the oil emissions in particular of uncombusted hydrocarbons must be measured, and this must be carried out at high speed over a great mass range in order to be able to obtain an impression even of processes occurring internally in the engine with sufficient dynamics.

This involves in particular the determination of oil emissions that are caused by various mechanisms. On the one hand there is evaporation, which in particular occurs with greater probability for higher-volatility molecules than for low-volatility molecules, depending in turn on the thermal energy. Another important mechanism is a parasitic flow in the combustion chamber (reverse blow-by), which represents a compensating gas flow and can be encountered in the reciprocating piston engine, in particular in the region of the piston rings and the piston grooves. It leads into the combustion chamber and thereby carries oil with it in the form of droplets. Finally, there is another important mechanism, that of oil being scraped off and/or thrown off by mechanical forces, so that the oil is torn out in the form of droplets of the oil and gets into the combustion chamber or the exhaust-gas flow.

Various measuring principles are known from the relevant prior art. A first measuring principle is based on chemiluminescence or UV fluorescence for the analysis of oil combustion residues and/or tracer substances. In the case of this measuring principle, the oil consumption can only be dependably measured if the oil constituents are completely converted into combustion residues, for example in the form of sulphur dioxide SO2. In principle, depending on the mixture forming parameters, a sufficient amount of oxygen or thermal energy is not available reliably for this in the combustion exhaust gas. Consequently, an oxidation furnace is therefore additionally provided to ensure complete combustion. An operating pressure which must not deviate too much from the ambient pressure is required for the combustion. In order to ensure a frictionless sample gas transfer, this operating pressure may only have a small pressure difference from the location from which the gas is taken. This may lead to restrictions with respect to the dynamics. Furthermore, the furnace itself represents a considerable low-pass in the measuring chain that restricts the applicability for dynamic measuring tasks. A further major disadvantage of this measuring principle is that detectors for UV fluorescence in particular have a pronounced cross-sensitivity with respect to other combustion residues or exhaust-gas constituents, so that signals that are not ascribable to the actual lubricating oil cause a falsification of the measuring results.

There is a further known measuring principle, in which the measuring gas is analyzed by mass spectrometry for oil combustion residues and/or tracer substances. This has the advantage over the aforementioned principle of lower cross-sensitivity with respect to further combustion residues or other exhaust-gas constituents. However, it must similarly be operated with a furnace for post-combustion. This gives rise to the same disadvantages with respect to the dynamics as in the case of the previously described method.

A further measuring principle is based on radioactivity. This involves collecting a radioactive element previously incorporated in the hydrocarbon chains of the lubricating oil by means of a filter or a condensate trap, and finally measuring it by means of a radioactivity detector. The handling of radioactive sources requires particular care and is therefore laborious. Moreover, the measuring result is influenced by the filtering characteristics or the capability of the condensate trap to form a corresponding condensate. Furthermore, it has been found that, if there is a lack of thermal energy, oil droplets such as occur in particular in the coasting mode of the engine do not reach the collection point, but are already deposited beforehand on walls of the line. Consequently, a falsification of the measuring result in the direction of lower values occurs.

A further measuring principle is known from DE 10 2004 001 514, in which uncombusted constituents of the lubricating oil are fed to a high-pass mass filter configured as an electrical multipole and are subsequently subjected to mass spectrometry. The measuring device itself has high dynamics, and to this extent meets requirements. However, its performance with respect to the detection of oil emissions in the form of droplets is unsatisfactory.

SUMMARY OF THE INVENTION

An object of the invention is providing an improved measuring device which, with continued high dynamics, allows robust detection in terms of the operating point even of oil emissions, specifically both in the form of vapors and in the form of droplets.

The way in which this is achieved according to the invention lies in the features broadly described below. Advantageous developments are described in the detailed embodiments below.

In the case of a multiple oil-emission measuring device for hydrocarbon emissions in an exhaust-gas mixture comprising an exhaust-gas probe with a transfer capillary and a measuring channel with an ion source, a filtering device with a measuring device, the filtering device preferably having a setting device for determining a passband range of a lubricating oil fraction to be measured, and the measuring device being a broadband measuring device, which preferably carries out a global measurement of the concentration of the molecules in one step over the passband range, it is provided according to the invention that the transfer capillary has at its tip a droplet-catching device, which has a short throttle segment and a transfer segment, which adjoins the throttle segment in the direction of flow and is at least ten times longer, and the measuring device is connected to an analyzing device, the analyzing device comprising a classifier for oil constituents in the form of vapors and oil constituents in the form of droplets.

The invention is based on the idea of making a quantifiable differentiation between oil emissions in the form of vapors and oil emissions in the form of droplets by means of the classifier. It is possible by means of this classifier to carry out a differentiation with regard to the vapor or droplet oil emissions. In addition, statements about the origination of the oil emissions can be made, whereby unnecessary oil consumption can be detected and corresponding measures for its reduction can be initiated. This classification with regard to emissions in the form of vapors or in the form of droplets would in itself be worthless, however, if emissions in the form of droplets were not detected sufficiently dependably. Therefore, the invention provides a combination with a specially designed exhaust-gas probe, which on account of its design is particularly suitable for the detection (also) of oil emissions in the form of droplets. Since, thanks to the good detection also of oil emissions in the form of droplets, it is irrelevant for the subsequent examination whether the oil emissions take place from the vapor or as an aerosol in the form of droplets, the determining device according to the invention is also robust with respect to operating point variations, with the accompanying shift between oil emissions in the form of vapors and oil emissions in the form of droplets, depending on thermal energy. By the combination of these measures, the invention consequently provides a determination of the oil emissions that is dynamic, accurate and, thanks to the dependable detection of emissions in the form of droplets, also robust in terms of the operating point.

A calibrator is expediently provided for the classifier, the calibrator having a first memory for reference data of oil constituents in the form of vapors and a second memory for reference data of oil constituents in the form of droplets. In this way, the classifier can be adapted easily and accurately to the spectra of the oil emission constituents to be analyzed. By storing appropriate data in the first and second memories, in this way an adaptation to other engines or other types of oil can also be easily performed.

For this purpose, the calibrator is preferably assigned a matched filter.

The matched filter is expediently designed for the detection of oil constituents in the form of vapors or oil constituents in the form of droplets. In this way, the type of lubricating oil emission can be determined better. This may involve the matched filter making use of findings with respect to the weighting of various fields/subfields. If for example a high proportion of low-volatility lubricating oil constituents correlates with a more moderate proportion of high-volatility lubricating oil constituents, this indicates a loss of oil due to scraping off or throwing off. Conversely, a predominant occurrence of high-volatility lubricating oil constituents as compared with low-volatility lubricating oil constituents indicates an emission based on evaporation. A correlation of the proportions of high-volatility lubricating oil constituents with high- and low-volatility lubricating oil constituents allows a statement to be made about the kind of originating mechanism. The matched filter makes this possible in a reliable and automated way.

Advantageously arranged on the exhaust-gas probe is a second measuring channel, which is connected to a determining device for combusted hydrocarbons. This provides a second measuring channel, which along with the uncombusted hydrocarbons determined by the analyzing device also takes into account the combusted hydrocarbons. Consequently, a comprehensive picture of the oil emissions can be achieved. Advantageously provided for this purpose is a totalizer, which determines a value for an overall emission from the values of the measuring device with the analyzing device on the one hand and from the values of the determining device on the other hand. In this way, a particularly robust measurement is made possible, since for example operating point-dependent shifts of oil emissions from uncombusted hydrocarbons to combusted hydrocarbons (or vice versa) are detected by the totalizer. A falsification of the measuring result on account of combustion processes of the hydrocarbons is thereby avoided.

Particularly advantageously, a vacuum pump is provided for the transfer channel. It is preferably set in such a way that a flow velocity of at least 100 m/s, preferably between 130 and 200 m/s, is obtained at the tip of the droplet-catching device. Thanks to this high velocity, a reliable detection of emissions in the form of droplets is ensured. This is independent of the operating point, and in particular also in respect of low-energy coasting operating points, which in the case of measuring principles according to the prior art sometimes led to considerable falsifications.

BRIEF DESCRIPTION OF THE DRAWINGS

The invention is explained in more detail below with reference to the accompanying drawing, in which an advantageous exemplary embodiment is represented and in which:

FIG. 2 shows a representation of a detail of an exhaust-gas probe with a measuring channel according to the exemplary embodiment;

FIGS. 3 a, b and c show a mass spectrogram to illustrate an operating principle of a classifier.

DETAILED DESCRIPTION OF THE DRAWINGS

Figure 1:
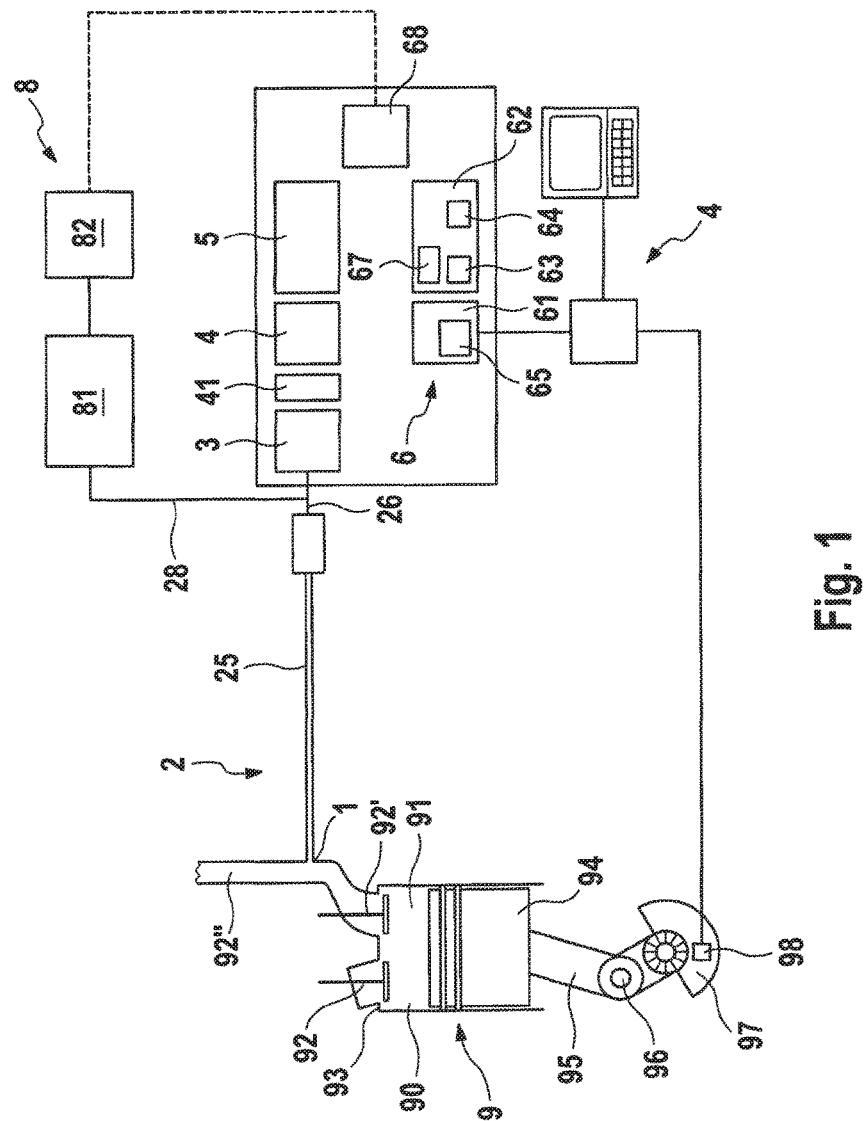
FIG. 1 shows a representation of an overview of a device according to an exemplary embodiment of the invention.

In FIGS. 1 and 2, an exemplary embodiment of a determining device according to the invention is represented. The determining device serves for determining oil emissions, to put it more generally for determining emissions of uncombusted hydrocarbons (HCs) that originate from an internal combustion engine. The exemplary embodiment represented is an internal combustion engine 9 based on the reciprocating piston principle, but the exemplary embodiment of the invention is not restricted to this. The engine 9 comprises at least one cylinder 90, in which a piston is guided movably up and down. Formed above the piston is a combustion chamber 91, to which fresh gas is fed by way of a valve 92 and from which exhaust gas is discharged into an exhaust-gas pipe 92" by way of a valve 92'. The piston 94 is connected to a crankshaft journal 96 of a crankshaft 97 by way of a connecting rod 95. Arranged on the crankshaft 97 is an angle encoder 98, which emits a measuring signal for the crankshaft position and rotational speed.

The internal combustion engine 9 is in fact of a conventional design, so that there is no need for a more detailed description. As a special feature, it has on the exhaust-gas pipe 92" an exhaust-gas probe 1, to which a transfer capillary 2 is connected and which is connected to a filter device 3 and also a measuring device 4. In the case of an alternative exemplary embodiment that is not represented, the exhaust-gas probe 1 leads through the wall of the cylinder head. It has in relation to the cylinder head a constricted diameter, which widens in multiple stages away from the cylinder head. At a region with a wide diameter, an inlet of the transfer capillary 2 is connected.

The transfer capillary 2 has at its front tip 21, by which it is connected to the exhaust-gas pipe 92", a droplet-catching device 22. This consists of a throttle segment 23, which is arranged directly in the mouth and has baffles 24 protruding obliquely at an angle of approximately 45° counter to the direction of flow. The baffles 24 are formed here to match the inner form of the transfer capillary 2; therefore, in the case of a circular transfer capillary 2, they have overall approximately the form of the shell of a truncated cone. Typical values for the diameter of the transfer capillary 2 are 0.5-2 mm, while in the throttle segment 23 of the droplet-catching device 22 the diameter is constricted to 0.2-0.5 mm.

The main region of the transfer capillary 2 extends as a pipe-like transfer segment, which in its rear region has a pressure stage 25 with a widened pipe diameter. This is approximately 2-6 mm. Connected to the rear end of the pressure stage 25 is a restriction capillary 26, which leads to an input connection of the filtering and measuring device 4, 5. The restriction capillary 26 has a considerably smaller diameter of 50-500 μm. This reduction in cross section has the effect that there is a division of the mass flow and also a decoupling in terms of pressure. The remaining mass flow is discharged to a vacuum pump 27, which is connected by way of an upstream vacuum tank 28 likewise to the rear end of the pressure stage 25 (see FIG. 2). With a pressure control 29, a desired vacuum is maintained with pressure stage 25 and in the transfer capillary 2.

Before it reaches the filtering device 4, the sample amount passed on from the restriction capillary 26 to the measuring channel is first fed to an ion source device 3. This is designed for ionizing the amount of gas flowing in. It is designed for example as an ionizer based on the SMB principle (Supersonic Molecular Beam). Arranged on the ion source 3, directly adjoining in the direction of flow, is the filtering device 4. Assigned to it is a setting device 41, which can be used to set a mass range that is allowed to pass through by the filtering device 4. The filtering device 4 consequently acts as a mass filter that only allows ions in a desired bandpass range of the mass spectrum to pass and filters out the rest. The filtering device 4 may for example be formed as a quadrupole filter. The construction of quadrupole filters is generally known in the prior art and need not be explained any further here.

Further downstream of the filtering device 4 in the direction of flow is the measuring device 5. The measuring device 5 comprises a detector and a mass separator. This measuring device allows a broadband quasi-simultaneous measurement of the intensity distribution of the ions over the specified bandpass range. The measuring signal thus obtained is an intensity sequence signal and is transmitted to an analyzing device 6. The measuring device 5 is enabled to detect the complete spectrum over the desired bandpass range by high-speed scanning with high dynamics and resolution.

The analyzing device 6 comprises a classifier 61, which acts together with a calibrator 62. The calibrator 62 comprises a first memory 63 and also a second memory 64. Contained in the first memory 63 are reference data on the spectral distribution of oil constituents in the form of vapors and contained in the second memory 64 are reference data on the spectral mass distribution of oil constituents in the form of droplets. Consequently, the calibrator 62 allows the classifier 61 to be set in such a way that it differentiates and evaluates in the measuring results of the measuring device 5 the oil constituents in the form of vapors on the one hand and the oil constituents in the form of droplets on the other hand.

Preferably, the formation of subfields is provided for the differentiation of oil constituents in the form of vapors and oil constituents in the form of droplets. Such a subfield is shown in the upper representation in FIG. 3. Two subfields are represented by dashed lines, a larger one (in the range of 170-380 m/z) and a smaller one (in the range of 170-270 m/z). It should be noted that in this case the subfields overlap, but they may also be separate from one another. The small subfield stands here for the high-volatility fraction, while the large subfield stands for the sum of the high- and low-volatility fractions.

A matched filter 65 is expediently provided for the evaluation, in particular with weighting of various fields or subfields that can be set. It forms part of the classifier 61 and likewise acts together with the calibrator 62, in order in this way to carry out an assignment of the determined mass spectra to predetermined originating mechanisms while taking into account the intensity sequences. It can in this way be determined for example whether the measured lubricating oil emissions are based on simple evaporation or on mechanical processes, such as scraping off or throwing off of the oil from the inner wall of the cylinder 90. This is to be explained for one type of lubricating oil by way of example on the basis of FIGS. 3 *a-c* (in other cases they may be different mass limits). For this determination, use is made of the finding that high- and low-volatility lubricating oil fractions generally get into the lubricating oil emissions in different ways. The high-volatility lubricating oil fractions generally get into the lubricating oil by evaporation, in particular from the inner wall of the cylinder (see, corresponding to FIG. 3 *a*, the small subfield surrounded by the gray dashed line in the diagram arranged thereabove). If, on the other hand, the lubricant emissions originate by scraping off on the inner wall of the cylinder 90, for example due to oil-derived carbon residues 99 on the piston 91 (see FIG. 3 *b*), the lubricating oil emission is of a broader band in the spectrum and ranges beyond molecular ions with a specific charge of over 350 m/z (see the subfield surrounded by the black dashed line). For the throwing off of the oil, in particular on piston rings of the piston 94 (see FIG. 3 *c*), in principle something similar is illustrated: also in this way both high- and low-volatility lubricating oil fractions get into the exhaust gas and are then detected as a lubricating oil emission. A correlation of the proportions of high-volatility lubricating oil fractions compared with high- and low-volatility lubricating oil fractions even allows a statement to be made about the type of originating mechanism. This takes place in an automated manner by means of the matched filter.

The determining device also has a further measuring branch 8 for determining combustion residues. It comprises a mass spectrometer 81, known per se, with a connected measuring device 82. This transmits the measuring data obtained to an interface module 68 of the analyzing device 6. This allows the analyzing device 6 also to take data on combusted oil constituents into account in the evaluation. This on the one hand allows a more comprehensive measuring result, and consequently an overview of the entire emissions of the oil, whether combusted or uncombusted. On the other hand, it allows the determination of the oil emission mechanism to be performed more accurately, since, in particular in the case of oil vapors, there is often an at least partial combustion of the oil emission, which thanks to the additional measuring branch 8 is consequently detected and taken into account in the further evaluation by means of the interface 68. The second measuring branch 8 is connected to the transfer capillary 2 by way of a second measuring channel 28.

Also provided is a totalizer 67. This serves the purpose of forming an overall value by taking as a basis the measured values from the measuring device 6 for the uncombusted hydrocarbon emissions and the measured values originating from the interface 68 for the combusted oil emissions.

Figure 4:
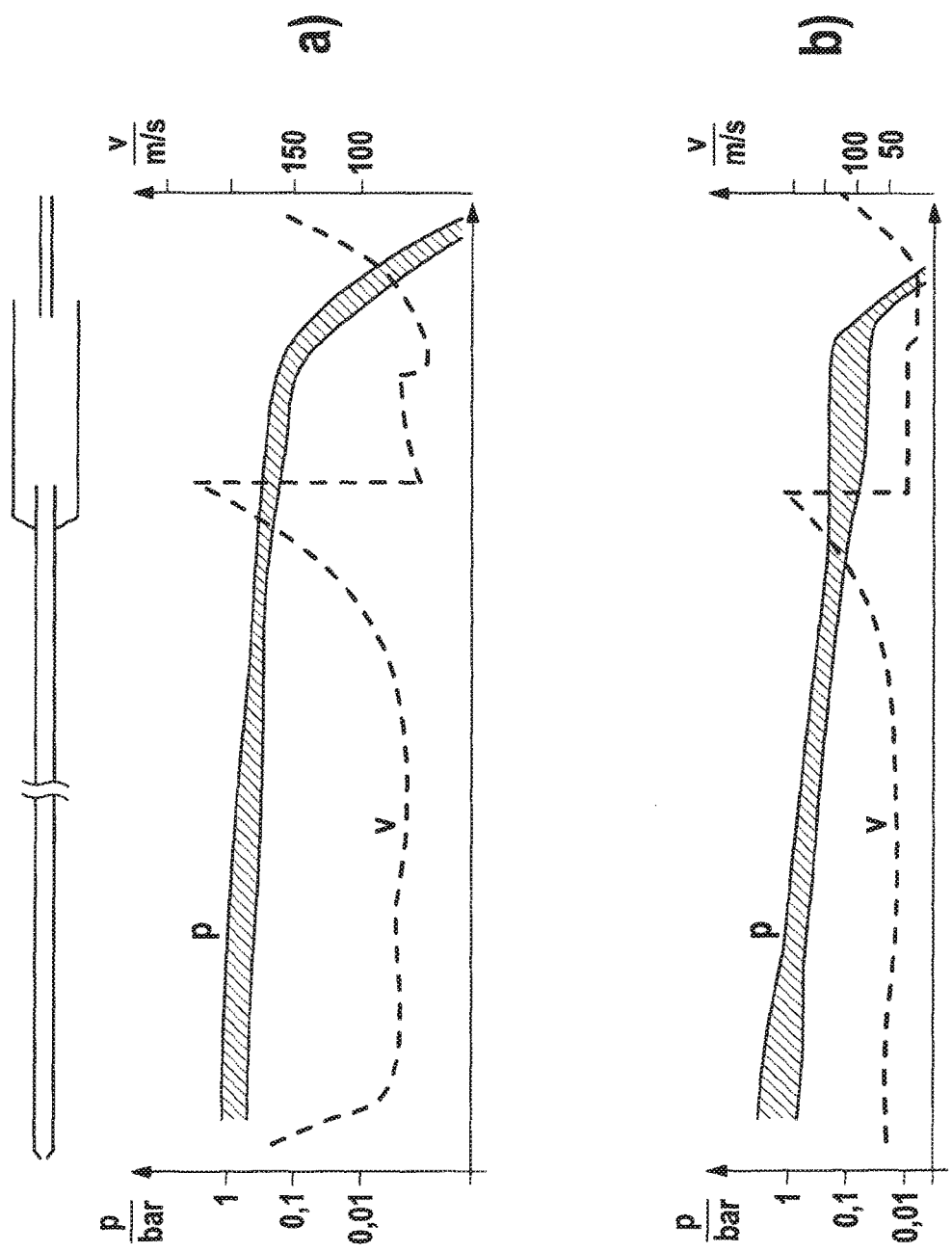
FIGS. 4 a and b show a diagram for comparison with an exhaust-gas probe according to the prior art.

For forming and maintaining the required vacuum in the transfer capillary 2, the vacuum pump 27 and the pressure control 29 are preferably designed for the purpose of generating a vacuum of approximately 0.3 bar absolute. On account of the geometrical conditions in the transfer capillary 2 with the pressure stage 25 and the line 22, a pressure profile such as that represented in FIG. 4 *a* is obtained. Also represented by a dashed line in FIG. 4 *a* is the flow velocity at the respective points in the transfer capillary 2 that is established with the pressure profile. It can be seen that, with the correspondingly set pressure, a very high flow velocity of approximately 150 m/s is achieved at the throttle segment 23 of the droplet-catching device 22. This is a considerable increase in comparison with known exhaust-gas sensors from the prior art, of which a comparative diagram is represented in FIG. 4 *b*. If the same vacuum is applied here at the end of the transfer capillary 2, only a velocity of less than 50 m/s (see dashed line) is obtained at the tip of the transfer capillary. With the droplet-catching device 22 according to the invention, thanks to the throttle segment 23 it is thus possible in a surprisingly simple and efficient way that a tripling of the inlet velocity can be achieved, which means a ninefold increase in the energy with which the droplets are entrained. This considerably improves the capability of the probe to "capture" the droplets, so that the quality of the measuring results is increased correspondingly significantly.

The invention claimed is:

1. A multiple oil-emission device for hydrocarbon emissions in an exhaust-gas mixture comprising an exhaust-gas probe with a transfer capillary and a measuring channel with an ion source, a filter, and a measuring sensor, the filter comprising a setter for setting a passband range according to a lubricating oil fraction to be measured, the measuring sensor being a broadband measuring sensor, which carries out a global measurement of the concentration of the molecules in one step over the passband range, wherein the transfer capillary has at its tip a droplet-catching device, which has a short throttle segment and a transfer segment, which adjoins the throttle segment in the direction of flow and is at least ten times longer, and the measuring sensor is connected to an analyzer, which comprises a classifier for oil constituents in the form of vapors and oil constituents in the form of droplets, and a calibrator is provided for the classifier, the calibrator having a first memory for reference data of oil constituents in the form of vapors and a second memory for reference data of oil constituents in the form of droplets.

2. The device of claim 1, wherein the classifier comprises a matched filter for detection of oil constituents in the form of vapors and oil constituents in the form of droplets.

3. The device of claim 1, wherein, arranged on the exhaust-gas probe, is a second measuring channel, which is connected to a determining device for combusted hydrocarbons.

4. The device of claim 3, comprising a totalizer, which determines a value for an overall consumption from the values of the analyzer and the determining device.

5. The device of claim 1, wherein a vacuum pump is provided for the transfer channel, the vacuum pump being configured to generate a flow velocity of at least 100 m/s at the tip of the droplet-catching device.

6. The device of claim 5, wherein the vacuum pump is configured to generate a flow velocity of 130-200 m/s at the tip of the droplet-catching device.

7. A multiple oil-emission device for hydrocarbon emissions in an exhaust-gas mixture comprising an exhaust-gas probe with a transfer capillary and a measuring channel with an ion source, filter, and a measuring sensor, the filter comprising a setter for setting a passband range according to a lubricating oil fraction to be measured, the measuring sensor being a broadband measuring sensor, which carries out a global measurement of the concentration of the molecules in one step over the passband range, wherein the transfer capillary has at its tip a droplet-catching device, which has a short throttle segment and a transfer segment, which adjoins the throttle segment in the direction of flow and is at least ten times longer, and the measuring sensor is connected to an analyzer, which comprises a classifier for oil constituents in the form of vapors and oil constituents in the form of droplets, and the classifier comprises a matched filter for detection of oil constituents in the form of vapors and oil constituents in the form of droplets.

8. The device of claim 7, wherein a calibrator is provided for the classifier, the calibrator having a first memory for reference data of oil constituents in the form of vapors and a second memory for reference data of oil constituents in the form of droplets.

9. The device of claim 7, wherein, arranged on the exhaust-gas probe, is a second measuring channel, which is connected to a determining device for combusted hydrocarbons.

10. The device of claim 9, comprising a totalizer, which determines a value for an overall consumption from the values of the analyzer and the determining device.

11. The device of claim 7, wherein a vacuum pump is provided for the transfer channel, the vacuum pump being configured to generate a flow velocity of at least 100 m/s at the tip of the droplet-catching device.

12. The device of claim 11, wherein the vacuum pump is configured to generate a flow velocity of 130-200 m/s at the tip of the droplet-catching device.

13. A multiple oil-emission device for hydrocarbon emissions in an exhaust-gas mixture comprising an exhaust-gas probe with a transfer capillary and a measuring channel with an ion source, filter, and a measuring sensor, the filter comprising a setter for setting a passband range according to a lubricating oil fraction to be measured, the measuring sensor being a broadband measuring sensor, which carries out a global measurement of the concentration of the molecules in one step over the passband range, wherein the transfer capillary has at its tip a droplet-catching device, which has a short throttle segment and a transfer segment, which adjoins the throttle segment in the direction of flow and is at least ten times longer, and the measuring sensor is connected to an analyzer, which comprises a classifier for oil constituents in the form of vapors and oil constituents in the form of droplets, and arranged on the exhaust-gas probe, is a second measuring channel, which is connected to a determining device for combusted hydrocarbons.

14. The device of claim 13, wherein a calibrator is provided for the classifier, the calibrator having a first memory for reference data of oil constituents in the form of vapors and a second memory for reference data of oil constituents in the form of droplets.

15. The device of claim 13, wherein the classifier comprises a matched filter for detection of oil constituents in the form of vapors and oil constituents in the form of droplets.

16. The device of claim 13, comprising a totalizer, which determines a value for an overall consumption from the values of the analyzer and the determining device.

17. The device of claim 13, wherein a vacuum pump is provided for the transfer channel, the vacuum pump being configured to generate a flow velocity of at least 100 m/s at the tip of the droplet-catching device.

18. The device of claim 17, wherein the vacuum pump is configured to generate a flow velocity of 130-200 m/s at the tip of the droplet-catching device.

19. A multiple oil-emission device for hydrocarbon emissions in an exhaust-gas mixture comprising an exhaust-gas probe with a transfer capillary and a measuring channel with an ion source, filter, and a measuring sensor, the filter comprising a setter for setting a passband range according to a lubricating oil fraction to be measured, the measuring sensor being a broadband measuring sensor, which carries out a global measurement of the concentration of the molecules in one step over the passband range, wherein the transfer capillary has at its tip a droplet-catching device, which has a short throttle segment and a transfer segment, which adjoins the throttle segment in the direction of flow and is at least ten times longer, and the measuring sensor is connected to an analyzer, which comprises a classifier for oil constituents in the form of vapors and oil constituents in the form of droplets, and a vacuum pump is provided for the transfer channel, the vacuum pump being configured to generate a flow velocity of at least 100 m/s at the tip of the droplet-catching device.

20. The device of claim 19, wherein a calibrator is provided for the classifier, the calibrator having a first memory for reference data of oil constituents in the form of vapors and a second memory for reference data of oil constituents in the form of droplets.

21. The device of claim 19, wherein the classifier comprises a matched filter for detection of oil constituents in the form of vapors and oil constituents in the form of droplets.

22. The device of claim 19, wherein, arranged on the exhaust-gas probe, is a second measuring channel, which is connected to a determining device for combusted hydrocarbons.

23. The device of claim 22, comprising a totalizer, which determines a value for an overall consumption from the values of the analyzer and the determining device.

24. The device of claim 19, wherein the vacuum pump is configured to generate a flow velocity of 130-200 m/s at the tip of the droplet-catching device.

* * * * *